US012638462B2

(12) United States Patent
Ebrahim et al.

(10) Patent No.: US 12,638,462 B2
(45) Date of Patent: May 26, 2026

(54) STABLE REFERENCE MATERIALS FOR AUTOMATED HEMATOLOGY TESTING PLATFORMS

(71) Applicant: BIO-RAD LABORATORIES, INC., Hercules, CA (US)

(72) Inventors: Alireza Ebrahim, Laguna Niguel, CA (US); James Barry, Newport Beach, CA (US); Karl Devore, Coto De Caza, CA (US)

(73) Assignee: BIO-RAD LABORATORIES, INC., Hercules, CA (US)

( * ) Notice: Subject to any disclaimer, the term of this patent is extended or adjusted under 35 U.S.C. 154(b) by 868 days.

(21) Appl. No.: 17/795,012

(22) PCT Filed: Jan. 28, 2021

(86) PCT No.: PCT/US2021/015351
§ 371 (c)(1),
(2) Date: Jul. 25, 2022

(87) PCT Pub. No.: WO2021/154900
PCT Pub. Date: Aug. 5, 2021

(65) Prior Publication Data
US 2023/0062518 A1     Mar. 2, 2023

Related U.S. Application Data

(60) Provisional application No. 63/027,984, filed on May 21, 2020, provisional application No. 62/968,211, filed on Jan. 31, 2020.

(51) Int. Cl.
*G01N 33/96* (2006.01)
*G01N 33/49* (2006.01)

(52) U.S. Cl.
CPC ......... *G01N 33/96* (2013.01); *G01N 33/4915* (2013.01); *G01N 2496/05* (2013.01); *Y10T 436/101666* (2015.01); *Y10T 436/106664* (2015.01)

(58) Field of Classification Search
CPC .. G01N 33/49; G01N 33/4915; G01N 33/492; G01N 33/96; G01N 2496/05; Y10T 436/10; Y10T 436/101666; Y10T 436/106664
USPC ........... 436/8, 10, 16, 63, 69, 164, 166, 172; 422/73, 82.05
See application file for complete search history.

(56) References Cited

U.S. PATENT DOCUMENTS

| | | | | |
|---|---|---|---|---|
| 5,432,089 A | * | 7/1995 | Ryan | G01N 15/1012 436/63 |
| 5,858,790 A | | 1/1999 | Kim et al. | |
| 5,874,310 A | * | 2/1999 | Li | G01N 33/80 436/63 |
| 6,200,500 B1 | * | 3/2001 | Ryan | G01N 33/5094 436/16 |
| 7,109,036 B2 | * | 9/2006 | Ortiz | G01N 15/12 436/16 |
| 7,195,919 B2 | * | 3/2007 | Jacobs | C12N 5/0641 436/66 |
| 9,714,897 B2 | | 7/2017 | Kim et al. | |
| 10,753,846 B2 | | 8/2020 | Kim et al. | |
| 11,686,661 B2 | * | 6/2023 | Kim | G01N 15/1459 436/8 |
| 12,038,369 B2 | * | 7/2024 | Kim | G01N 33/5047 |
| 2003/0113733 A1 | | 6/2003 | Khan et al. | |
| 2003/0175410 A1 | | 9/2003 | Campbell et al. | |
| 2005/0255447 A1 | | 11/2005 | Ortiz et al. | |
| 2008/0111272 A1 | | 5/2008 | Burgess et al. | |
| 2010/0047905 A1 | * | 2/2010 | Ryan | G01N 33/96 435/325 |
| 2010/0086962 A1 | * | 4/2010 | Hunsley | G01N 33/96 435/29 |
| 2010/0112723 A1 | * | 5/2010 | Battrell | G01N 33/53 422/68.1 |
| 2011/0089340 A1 | | 4/2011 | Merchez et al. | |
| 2016/0258856 A1 | | 9/2016 | Kim et al. | |

FOREIGN PATENT DOCUMENTS

WO      WO 2016/130489      8/2016

OTHER PUBLICATIONS

Slingshotbio.com website, accessed Oct. 18, 2023, pp. 1-11.
Anonymous "Hematology and Coagulation Controls" Bio-Rad Laboratories, 2016, pp. 1-15, retrieved from the Internet: https://bio-rad.com/webroot/web/pdf/cdg/literature/Q1523_Hematology.pdf.
Longanbach, S. et al. "Automated Blood Cell Analysis" 2016, pp. 208-227.
Supplementary European Search Report from Application No. EP21747359, Jan. 26, 2024, pp. 1-12.
Written Opinion in International Application No. PCT/US2021/015351, Apr. 7, 2021, pp. 1-8.
Vis, J. Y. et al. "Verification and quality control of routine hematology analyzers" *International Journal of Laboratory Hematology*, 2016, pp. 100-109, vol. 38, Suppl. 1.

* cited by examiner

*Primary Examiner* — Maureen Wallenhorst
(74) *Attorney, Agent, or Firm* — SALIWANCHIK, LLOYD & EISENSCHENK

(57) ABSTRACT

This invention describes a method for preparation of stable hematology reference materials by producing synthetic hydrogel blood cell surrogates, which mimic human blood components in size, morphology, performance and functionality when analyzed using an automated hematology analyzer employing multiple detection technologies. Different hydrogel particles can be combined and mixed to prepare multi-parameter and multi-level hematology reference materials, which could be used for calibration, linearity verification, proficiency evaluation, and routine performance monitoring of modern automated hematology analyzers. These hydrogel particles can also be combined with processed and stabilized human blood components to prepare the reference materials of this invention.

23 Claims, 7 Drawing Sheets

Lot Number: 133182410      LIS Status: Not Sent
Source: BCI   Instrument DxH800   Shift: 1
Control Type: COULTER® 6C Cell   Tube Pos ID: 00016   System Messages:
Level: Level2
Excluded: No   Presented By: SYSTEM
Presentation: Cassette   Reviewed By: Admin

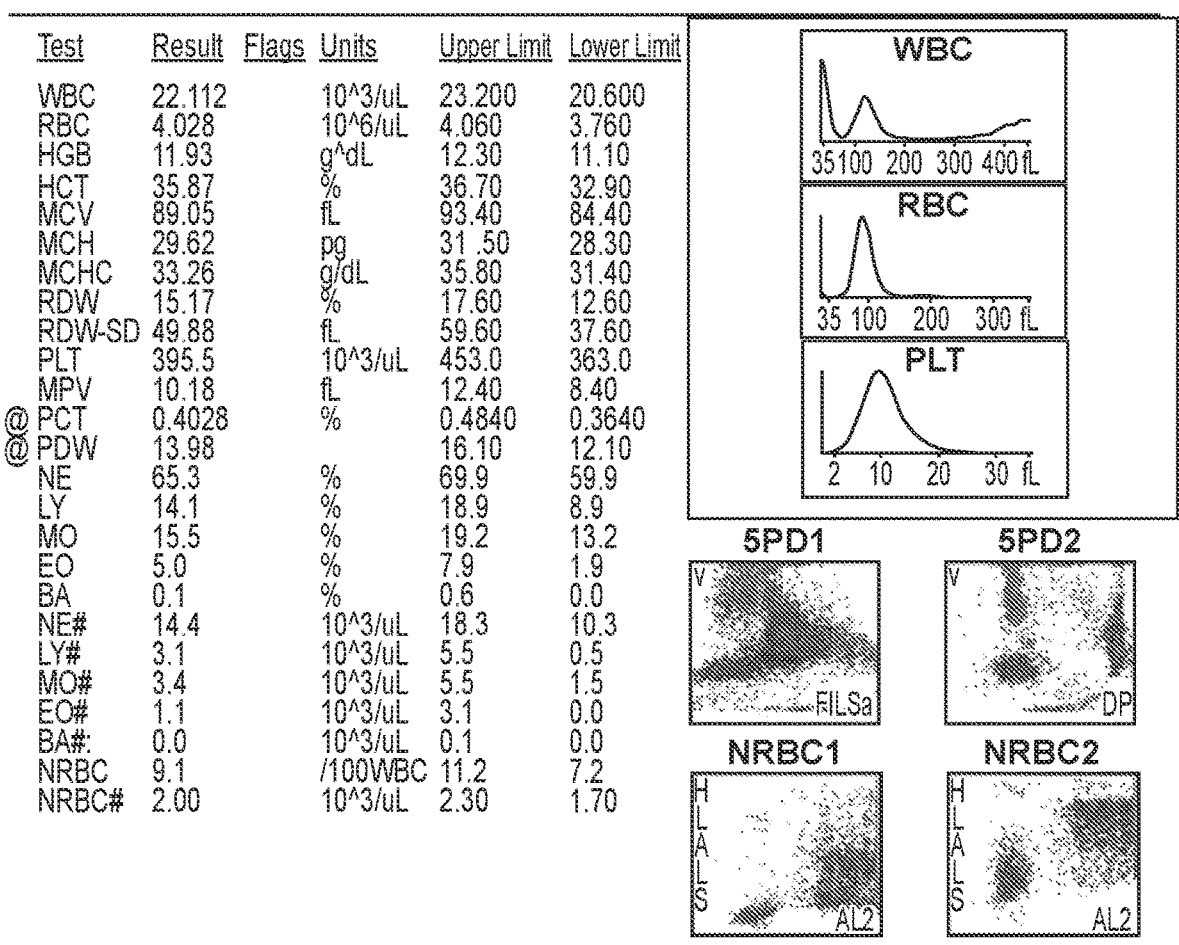

| Test | Result | Flags | Units | Upper Limit | Lower Limit |
|------|--------|-------|-------|-------------|-------------|
| WBC | 22.112 | | 10^3/uL | 23.200 | 20.600 |
| RBC | 4.028 | | 10^6/uL | 4.060 | 3.760 |
| HGB | 11.93 | | g^dL | 12.30 | 11.10 |
| HCT | 35.87 | | % | 36.70 | 32.90 |
| MCV | 89.05 | | fL | 93.40 | 84.40 |
| MCH | 29.62 | | pg | 31.50 | 28.30 |
| MCHC | 33.26 | | g/dL | 35.80 | 31.40 |
| RDW | 15.17 | | % | 17.60 | 12.60 |
| RDW-SD | 49.88 | | fL | 59.60 | 37.60 |
| PLT | 395.5 | | 10^3/uL | 453.0 | 363.0 |
| MPV | 10.18 | | fL | 12.40 | 8.40 |
| @ PCT | 0.4028 | | % | 0.4840 | 0.3640 |
| @ PDW | 13.98 | | | 16.10 | 12.10 |
| NE | 65.3 | | % | 69.9 | 59.9 |
| LY | 14.1 | | % | 18.9 | 8.9 |
| MO | 15.5 | | % | 19.2 | 13.2 |
| EO | 5.0 | | % | 7.9 | 1.9 |
| BA | 0.1 | | % | 0.6 | 0.0 |
| NE# | 14.4 | | 10^3/uL | 18.3 | 10.3 |
| LY# | 3.1 | | 10^3/uL | 5.5 | 0.5 |
| MO# | 3.4 | | 10^3/uL | 5.5 | 1.5 |
| EO# | 1.1 | | 10^3/uL | 3.1 | 0.0 |
| BA#: | 0.0 | | 10^3/uL | 0.1 | 0.0 |
| NRBC | 9.1 | | /100WBC | 11.2 | 7.2 |
| NRBC# | 2.00 | | 10^3/uL | 2.30 | 1.70 |

FIG. 2

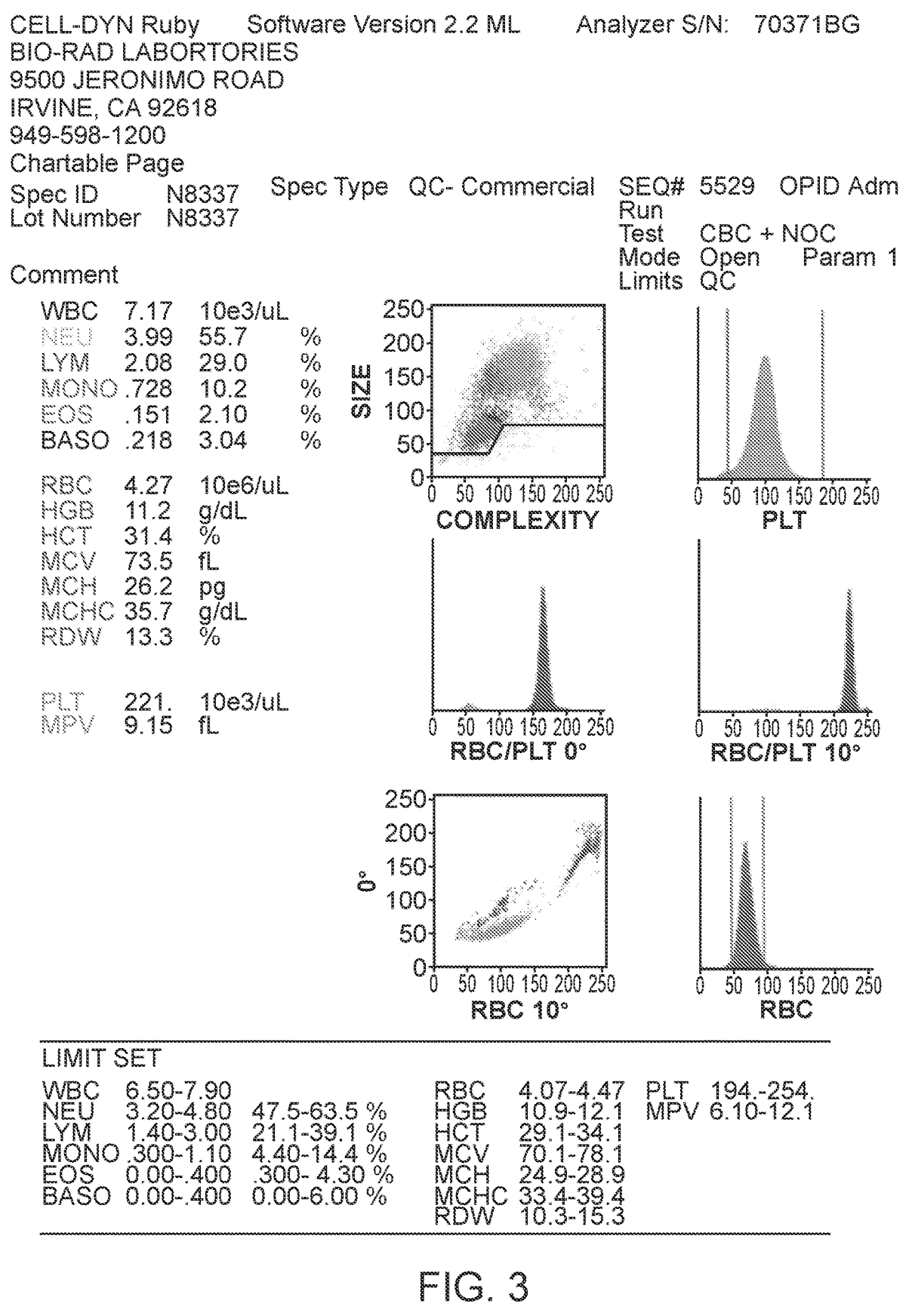

CELL-DYN Ruby    Software Version 2.2 ML    Analyzer S/N:   70371BG
BIO-RAD LABORTORIES
9500 JERONIMO ROAD
IRVINE, CA 92618
949-598-1200
Chartable Page Spec ID       N8337    Spec Type   QC- Commercial    SEQ# 5529   OPID Adm
Lot Number    N8337                                  Run
                                                     Test    CBC + NOC
                                                     Mode    Open    Param 1
Comment                                              Limits  QC

| | | | |
|---|---|---|---|
| WBC | 7.17 | 10e3/uL | |
| NEU | 3.99 | 55.7 | % |
| LYM | 2.08 | 29.0 | % |
| MONO | .728 | 10.2 | % |
| EOS | .151 | 2.10 | % |
| BASO | .218 | 3.04 | % |
| | | | |
| RBC | 4.27 | 10e6/uL | |
| HGB | 11.2 | g/dL | |
| HCT | 31.4 | % | |
| MCV | 73.5 | fL | |
| MCH | 26.2 | pg | |
| MCHC | 35.7 | g/dL | |
| RDW | 13.3 | % | |
| | | | |
| PLT | 221. | 10e3/uL | |
| MPV | 9.15 | fL | |

COMPLEXITY    PLT

RBC/PLT 0°    RBC/PLT 10°

RBC 10°    RBC

LIMIT SET

| | | | | | | | |
|---|---|---|---|---|---|---|---|
| WBC | 6.50-7.90 | | RBC | 4.07-4.47 | PLT | 194.-254. | |
| NEU | 3.20-4.80 | 47.5-63.5 % | HGB | 10.9-12.1 | MPV | 6.10-12.1 | |
| LYM | 1.40-3.00 | 21.1-39.1 % | HCT | 29.1-34.1 | | | |
| MONO | .300-1.10 | 4.40-14.4 % | MCV | 70.1-78.1 | | | |
| EOS | 0.00-.400 | .300- 4.30 % | MCH | 24.9-28.9 | | | |
| BASO | 0.00-.400 | 0.00-6.00 % | MCHC | 33.4-39.4 | | | |
| | | | RDW | 10.3-15.3 | | | |

FIG. 3

| Header-WB | | |
|---|---|---|
| SID | CONTROL5085 | |
| Aspiration Date/Time | | |
| Sample Type | CONTROL | |
| Rack & Position | 0.0 | |
| Cal Factors | Current | |
| FOR LABORATORY USE ONLY | | |

HGB Trans

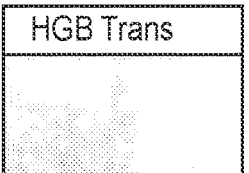

| Routine CBC | | | |
|---|---|---|---|
| WBC | 7.28 | | x10³ cells /µL |
| RBC | 4.12 | • | x10⁴ cells /µL |
| HGB | 11.4 | • | g/dL |
| HCT | 32.7 | • | % |
| MCV | 79.4 | • | fL |
| MCH | 27.7 | • | pg |
| MCHC | 34.9 | • | g/dL |
| CHCM | 32.0 | • | g/dL |
| CH | 25.3 | • | pg |
| RDW | 16.0 | • | % |
| HDW | 2.60 | • | g/dL |
| PLT | 228 | | x10³ cells /µL |
| MPV | 8.1 | | fL |

| Routine WBC Differential | % | | | # | | |
|---|---|---|---|---|---|---|
| WBC | | | | 7.28 | | x10³ cells /µL |
| Neut | 60.2 | • | | 4.38 | • | x10³ cells /µL |
| Lymph | 25.5 | • | | 1.86 | • | x10³ cells /µL |
| Mono | 8.2 | • | | 0.60 | • | x10³ cells /µL |
| Eos | 1.6 | • | | 0.11 | • | x10³ cells /µL |
| Baso | 0.3 | | | 0.02 | | x10³ cells /µL |
| LUC | 4.2 | • | | 0.31 | • | x10³ cells /µL |
| NRBC | 0.0 | | | 0.00 | | x10⁹cells /L |
| LI | | | | 1.36 | | |
| MPXI | | | | -12.2 | | |
| WPCP | | | | 7.30 | | x10³ cells /µL |

| Routine Retic | % | | | # | | |
|---|---|---|---|---|---|---|
| Retic | 3.37 | | | 138.8 | | x10⁹ cells /L |
| CHr | | | | 23.0 | | pg |
| CHm | | | | 25.1 | | pg |

| Additional Routine Parameters | | |
|---|---|---|
| %Blast Suspect | 0.1 | |
| %Hyper | 0.2 | |
| %Hypo | 6.8 | |
| %Macro | 0.2 | |
| %Micro | 5.7 | |
| RBC Fragments | 0.01 | x10⁶ cells /µL |
| RBC Ghosts | 0.07 | x10⁶ cells /µL |
| Neut X | 54.0 | |
| Neut Y | 73.6 | |
| MNx | | |
| MNy | 6.0 | |
| %MN | 0.3 | |
| %MN | 1.4 | |
| Cellular HGB | 10.5 | g/dL |

Baso Rate

Perox Rate

Morphology Flags

FIG. 4

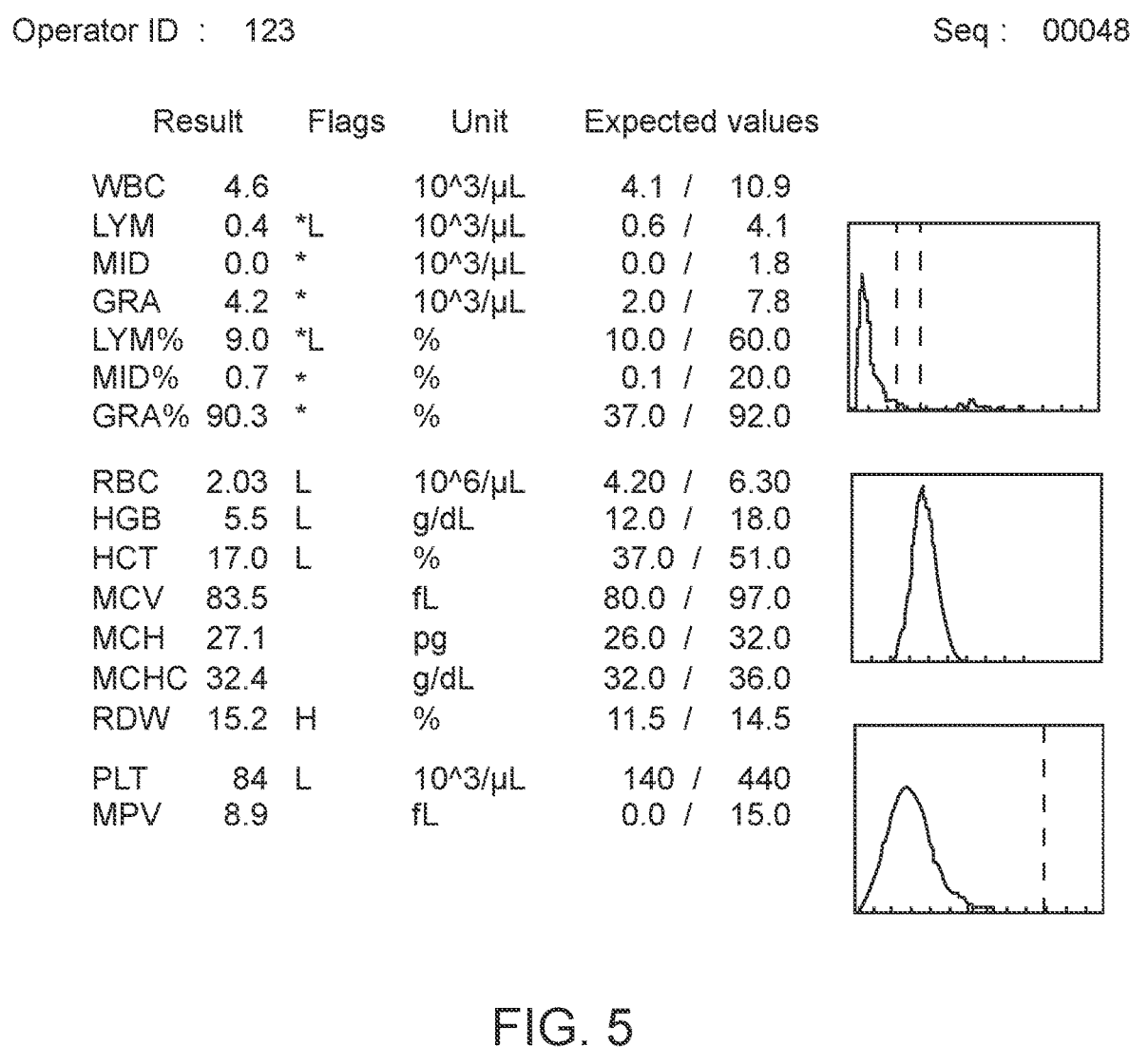

Operator ID : 123         Seq : 00048

| | Result | Flags | Unit | Expected values | |
|---|---|---|---|---|---|
| WBC | 4.6 | | 10^3/µL | 4.1 / | 10.9 |
| LYM | 0.4 | *L | 10^3/µL | 0.6 / | 4.1 |
| MID | 0.0 | * | 10^3/µL | 0.0 / | 1.8 |
| GRA | 4.2 | * | 10^3/µL | 2.0 / | 7.8 |
| LYM% | 9.0 | *L | % | 10.0 / | 60.0 |
| MID% | 0.7 | * | % | 0.1 / | 20.0 |
| GRA% | 90.3 | * | % | 37.0 / | 92.0 |
| | | | | | |
| RBC | 2.03 | L | 10^6/µL | 4.20 / | 6.30 |
| HGB | 5.5 | L | g/dL | 12.0 / | 18.0 |
| HCT | 17.0 | L | % | 37.0 / | 51.0 |
| MCV | 83.5 | | fL | 80.0 / | 97.0 |
| MCH | 27.1 | | pg | 26.0 / | 32.0 |
| MCHC | 32.4 | | g/dL | 32.0 / | 36.0 |
| RDW | 15.2 | H | % | 11.5 / | 14.5 |
| | | | | | |
| PLT | 84 | L | 10^3/µL | 140 / | 440 |
| MPV | 8.9 | | fL | 0.0 / | 15.0 |

FIG. 5

STABLE REFERENCE MATERIALS FOR AUTOMATED HEMATOLOGY TESTING PLATFORMS

CROSS-REFERENCE TO RELATED APPLICATION

This application is the U.S. national stage application of International Patent Application No. PCT/US2021/015351, filed Jan. 28, 2021.

BACKGROUND OF THE INVENTION

Quality control is a necessary and routine procedure in clinical hematology. Accuracy in the counting of cells in biological samples and being able to differentiate subpopulations of blood cells (e.g., platelets, lymphocytes, granulocytes, etc.) is dependent, in part, on the use of adequate control products. The subject invention provides a stable reference material for use in automated hematology testing platforms.

BRIEF SUMMARY OF THE INVENTION

Flow cytometry permits rapid separation, counting, and characterization of individual cells and can be used experimentally and clinically. Flow cytometry distinguishes cells on the basis of light scattering caused by cells within a liquid stream that is being analyzed. To distinguish cells, detectors are utilized to determine Forward Scatter (FSC) and Side Scatter (SSC). FSC correlates with the cell volume and is measured by a detector that is in line with the light beam being transmitted into the liquid stream. SSC is determined by measuring light scattering using detectors that are perpendicular (or substantially perpendicular) to the light being transmitted into the liquid stream. Different specific cell types exhibit different FSC and SSC which allows for the identification of each distinct cell type.

This invention involves preparing, combining, and mixing synthetic hydrogel blood cell surrogates in an isotonic pH neutral base matrix fluid in order to prepare multi-parameter and multi-level hematology reference materials (HRM). The HRM provided by the subject disclosure can be used for calibration, linearity verification, proficiency evaluation, and/or routine performance monitoring of modern automated hematology analyzers employing multiple detection technologies. The HRM described here comprises one or more synthetic components (for example, tuned hydrogel particles), one or more animal blood components, and/or one or more human blood components.

BRIEF DESCRIPTION OF THE DRAWINGS

FIGS. 1-4 are typical hematology reports generated by the automated hematology analyzers Sysmex XN 1000 (FIG. 1), Beckman-Coulter DxH 800 (FIG. 2), Abbott CELL-DYN Ruby (FIG. 3), and Siemens Advia 1220 (FIG. 4). These analyzers identify, measure, and enumerate various cellular blood components, and generate histograms, scattergrams, and cytograms for each blood sample analyzed. For example, the Sysmex XN 1000 generates 32 parameters, 2 histograms, and 5 scattergrams and the Beckman-Coulter DxH 800 generates 25 parameters, 3 histograms, and 4 scattergrams. The differences among the reports generated by these analyzers are due to the differences in technologies used by these manufacturers (absorption spectrophotometric, flow cytometric, and electrical impedance).

FIG. 5 is the hematology report generated using Abbott Cell-Dyn Emerald Hematology Analyzer for a typical HRM of this invention.

DETAILED DISCLOSURE OF THE INVENTION

Figure 1:
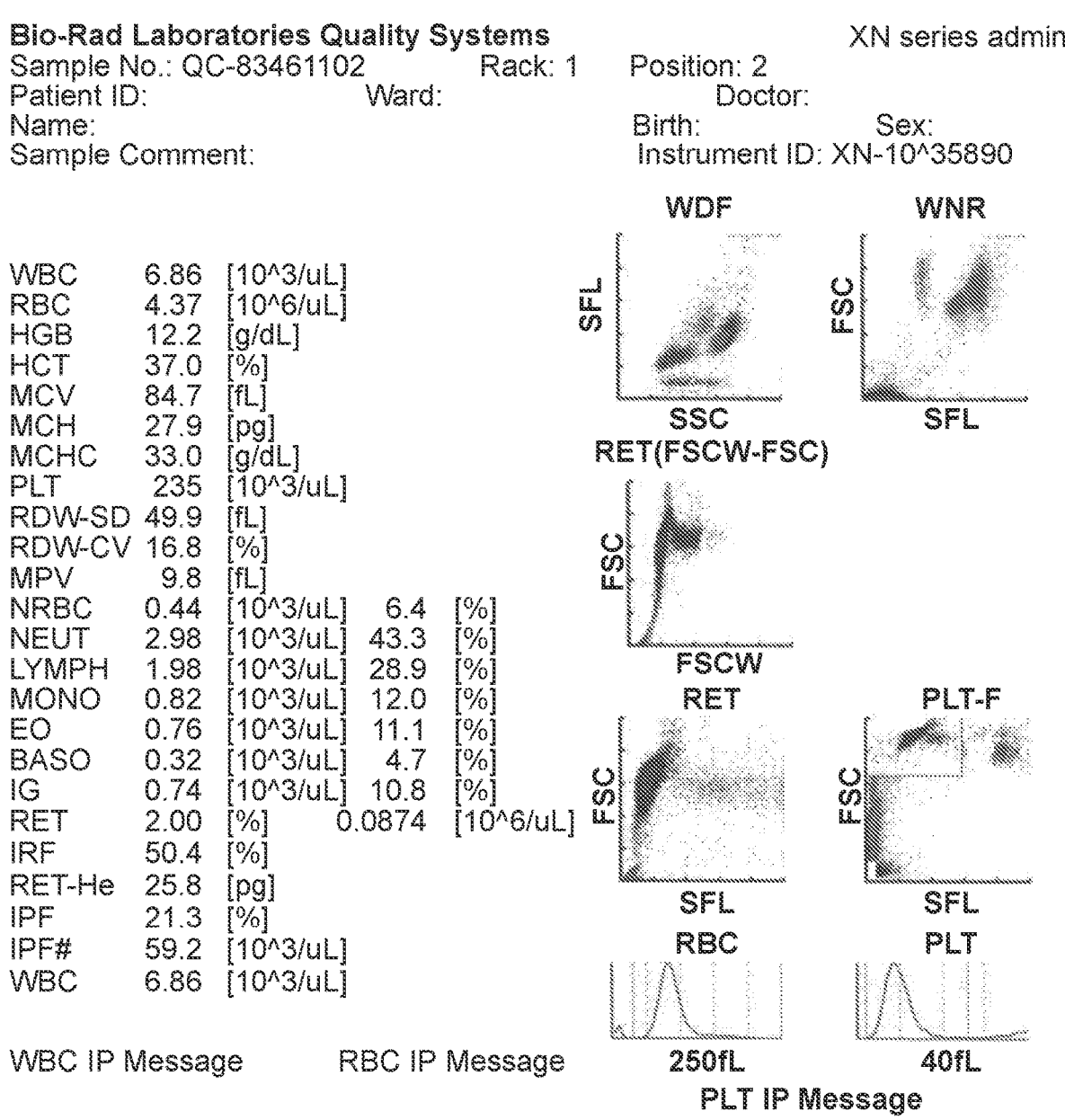
Figure 4:
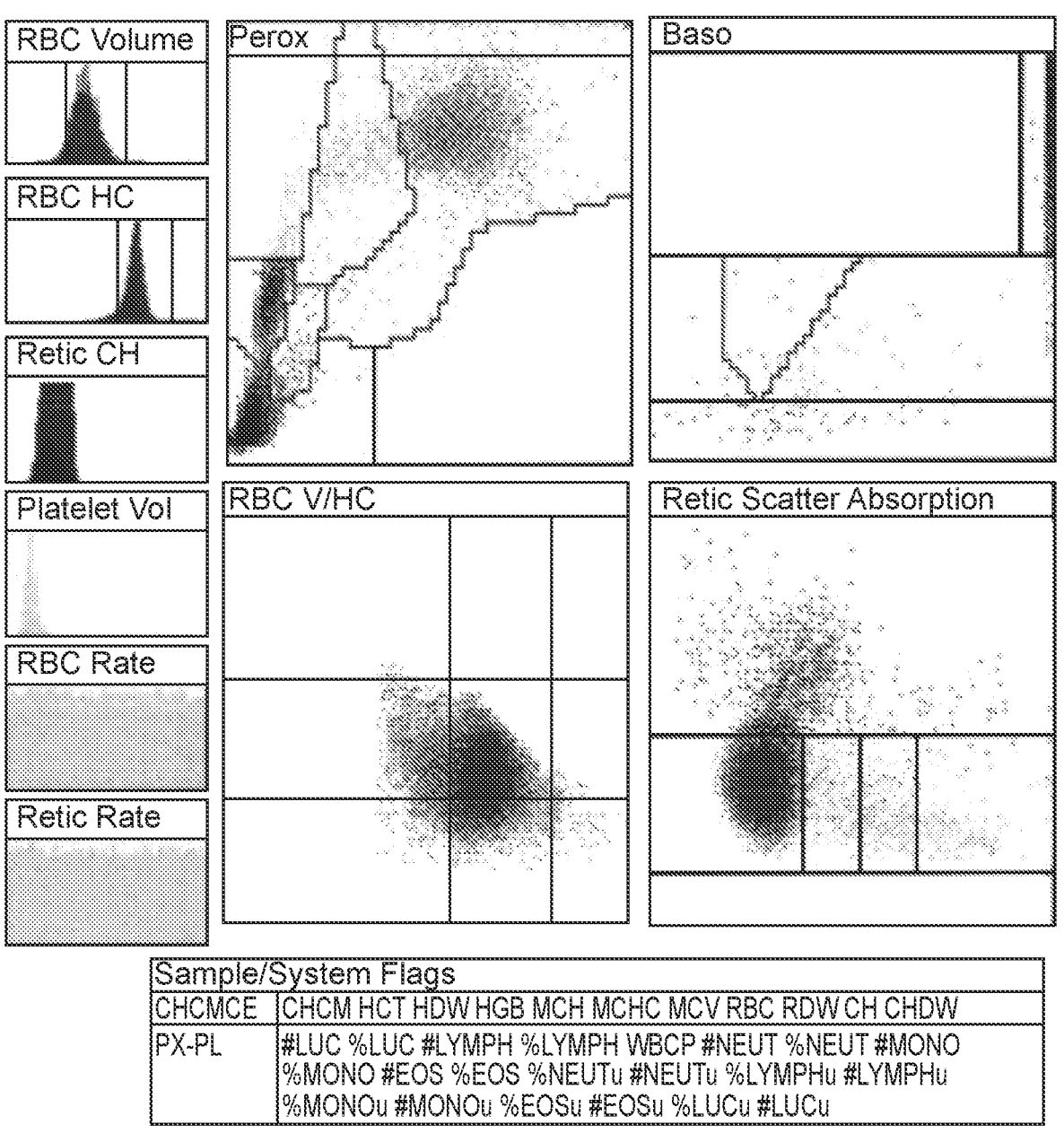

Flow cytometry permits rapid separation, counting, and characterization of individual cells and can be used experimentally and clinically. Flow cytometry distinguishes cells on the basis of light scattering caused by cells within a liquid stream that is being analyzed. To distinguish cells, detectors are utilized to determine Forward Scatter (FSC) and Side Scatter (SSC). FSC correlates with the cell volume and is measured by a detector that is in line with the light beam being transmitted into the liquid stream. SSC is determined by measuring light scattering using detectors that are perpendicular (or substantially perpendicular) to the light being transmitted into the liquid stream. Different specific cell types exhibit different FSC and SSC which allows for the identification of each distinct cell type.

As used herein, the singular forms "a", "an" and "the" are intended to include the plural forms as well, unless the context clearly indicates otherwise. Furthermore, to the extent that the terms "including", "includes", "having", "has", "with", or variants thereof are used in either the detailed description and/or the claims, such terms are intended to be inclusive in a manner similar to the term "comprising". The transitional terms/phrases (and any grammatical variations thereof) "comprising", "comprises", "comprise", "consisting essentially of", "consists essentially of", "consisting" and "consists" can be used interchangeably.

The term "about" or "approximately" means a range of up to 0-20%, 0 to 10%, 0 to 5%, or up to 1% of a given value. In the context of compositions or temperatures where the terms "about" or "approximately" are used, these compositions contain the stated amount of the ingredient with a variation (error range) of 0-10% around the value (X±10%). In the present disclosure, ranges are stated in shorthand, so as to avoid having to set out at length and describe each and every value within the range. Any appropriate value within the range can be selected, where appropriate, as the upper value, lower value, or the terminus of the range. For example, a range of 0.1-1.0 represents the terminal values of 0.1 and 1.0, as well as the intermediate values of 0.2, 0.3, 0.4, 0.5, 0.6, 0.7, 0.8, 0.9, and all intermediates ranges encompassed within 0.1-1.0, such as 0.2-0.5, 0.2-0.8, 0.7-1.0, etc. Values having at least two significant digits within a range are envisioned, for example, a range of 5-10 indicates all the values between 5.0 and 10.0 as well as between 5.00 and 10.00 including the terminal values.

This invention involves preparing, combining, and mixing blood cell surrogates (analogs) in an isotonic pH neutral suspension fluid in order to prepare multi-parameter and multi-level hematology reference materials (HRM). The HRM provided by the subject disclosure can be used for calibration, linearity verification, proficiency evaluation, and/or routine performance monitoring of modern automated hematology analyzers employing multiple detection technologies. The HRM described here comprises one or more synthetic components (for example, tuned hydrogel particles) and/or one or more biological components (e.g., one or more animal blood components, and/or one or more human blood components tuned to represent a specific cell type). Specifically excluded as a HRM is a biological sample obtained from human or non-human subjects that contain each of the components disclosed herein.

The components of the HRM are tuned so as to represent the cell type they represent (e.g., red blood cells, platelets, etc.) and the different components of the HRM can be mixed to arrive at a particular HRM. Furthermore, each component of the HRM is similar in size (for example shape, diameter and/or volume) to its naturally occurring counterpart regardless of whether it is prepared from an erythrocyte or is synthetic (e.g., a hydrogel particle). Each component of the HRM is also substantially similar, optically, to the cell type it represents and has one or more optical properties, such as a side scatter profile, a forward scatter profile or a secondary marker profile substantially similar to its human counterpart. In some embodiments, a one or more component of the HRM can be provided as an admixture comprising about 0.1% to about 99.9% biological component and about 0.1% to about 99.9% synthetic component, the percentages of which total 100% of for that particular component. By way of example, if the HRM component is the platelet component, 5% of the component can be biological and 95% of the component can be synthetic such that the total platelet component, for example total platelet cell number per microliter is 100% of the expected value of the HRM for platelet content.

Thus, the HRM comprises one or more of the following components:

Suspension Fluid: An aqueous isotonic solution with neutral pH containing various additives such as anti-microbial agents, surfactants, stabilizers, buffers, salts, enzyme inhibitors, albumin, and lipoprotein. In some embodiments, the suspension fluid comprises phosphate buffered saline solution and an aqueous solution of a plasma substance, such as an aqueous solution of serum lipid. Serum lipid comprises cholesterol, cholesterol esters and cholesterol which has been combined with one or more other compounds found in serum plasma and mixtures thereof (for example, lipoproteins and phospholipids, and mixtures thereof). The suspension fluid may also contain one or more of the proteins contained in plasma, such as albumin, lipoproteins, globulins, fibrinogens and mixtures thereof. As indicated above, the suspension fluid may also contain various additives such as anti-microbial agents, surfactants, stabilizers, buffers, salts, enzyme inhibitors.

Red Blood Cell (RBC) Component: Separated and washed human erythrocytes fixed with low concentration of a crosslinking agent such as glutaraldehyde or hydrogel particles similar in size (diameter and volume) to human red blood cells containing hemoglobin. The RBC component selected for inclusion in the HRM has one or more optical properties, for example, a side scatter profile, a forward scatter profile, etc. that is substantially similar to human RBC.

Platelet Component: Separated and washed goat erythrocytes fixed with high concentration of a crosslinking agent such as glutaraldehyde or hydrogel particles similar in size (diameter and volume) to human platelets. The platelet component selected for inclusion in the HRM has one or more optical properties, for example, a side scatter profile, a forward scatter profile, etc. that is substantially similar to human platelets.

Reticulocyte Component: Separated and washed human erythrocytes encapsulated with RNA using various encapsulation processes such as reversible osmotic lysis or electroporation followed by soft glutaraldehyde fixation or hydrogel particles similar in size (diameter and volume) to human reticulocytes containing RNA or tagged with a fluorescence dye used in reticulocyte testing. The reticulocyte component selected for inclusion in the HRM has one or more optical properties, for example, a side scatter profile, a forward scatter profile, etc. that is substantially similar to human reticulocytes.

Lymphocyte Component: Separated and washed chicken erythrocytes fixed with high concentration of a crosslinking agent such as glutaraldehyde or hydrogel particles similar in size to human lymphocytes, which are selectively tunable to have optical properties substantially similar to human lymphocytes (e.g., similar in diameter and volume). The lymphocyte component selected for inclusion in the HRM has one or more optical properties, for example, a side scatter profile, a forward scatter profile, etc. that is substantially similar to human lymphocytes.

Monocyte Component: Separated and washed turkey erythrocytes fixed with high concentration of a crosslinking agent such as glutaraldehyde or hydrogel particles similar in size to human monocytes, which are selectively tunable to have optical properties substantially similar to human lymphocytes. The monocyte component selected for inclusion in the HRM has one or more optical properties, for example, a side scatter profile, a forward scatter profile, etc. that is substantially similar to human monocytes.

Basophil Component: Separated and washed alligator erythrocytes fixed with high concentration of a crosslinking agent such as glutaraldehyde or hydrogel particles similar in size to human basophils, which are selectively tunable to have optical properties substantially similar to human basophils. The basophil component selected for inclusion in the HRM has one or more optical properties, for example, a side scatter profile, a forward scatter profile, etc. that is substantially similar to human basophils.

Neutrophil Component: Separated and washed alligator erythrocytes fixed with high concentration of a crosslinking agent such as glutaraldehyde or hydrogel particles similar in size to human neutrophils, which are selectively tunable to have optical properties substantially similar to human neutrophils. The neutrophil component selected for inclusion in the HRM has one or more optical properties, for example, a side scatter profile, a forward scatter profile, etc. that is substantially similar to human neutrophils.

Eosinophil Component: Separated and washed alligator erythrocytes fixed with high concentration of a crosslinking agent such as glutaraldehyde or hydrogel particles similar in size to human eosinophils, which are selectively tunable to have optical properties substantially similar to human eosinophils. The eosinophil component selected for inclusion in the HRM has one or more optical properties, for example, a side scatter profile, a forward scatter profile, etc. that is substantially similar to human eosinophils.

Immature Reticulocyte Component: Separated and washed human erythrocytes encapsulated with RNA or hydrogel particles similar in size to human reticulocytes containing large amount of RNA or hydrogel particles labeled with common dyes used for reticulocyte analysis. The immature reticulocyte component selected for inclusion in the HRM has one or more optical properties, for example, a side scatter profile, a forward scatter profile, etc. that is substantially similar to immature human reticulocytes.

Immature Granulocyte Component: Separated and washed alligator erythrocytes fixed with high concentration of a crosslinking agent such as glutaraldehyde or hydrogel particles similar in size to human immature granulocytes, which are selectively tunable to have optical properties substantially similar to human immature granulocytes. The immature granulocyte component selected for inclusion in the HRM has one or more optical properties, for example, a side scatter profile, a forward scatter profile, etc. that is substantially similar to immature human granulocytes.

Immature Thrombocyte Component: Separated and washed goat erythrocytes fixed with high concentration of a crosslinking agent such as glutaraldehyde or hydrogel particles similar in size to human platelets containing nucleic acid or labeled with common dyes used for immature thrombocyte analysis. The immature thrombocyte component selected for inclusion in the HRM has one or more optical properties, for example, a side scatter profile, a forward scatter profile, etc. that is substantially similar to immature human thrombocytes.

Nucleated Red Blood Cell Component: Separated and chicken erythrocytes fixed with high concentration of a crosslinking agent such as glutaraldehyde or hydrogel particles similar in size to nucleated red blood cells, which are selectively tunable to have optical properties substantially similar to human nucleated red blood cells. The nucleated RBC component selected for inclusion in the HRM has one or more optical properties, for example, a side scatter profile, a forward scatter profile, etc. that is substantially similar to nucleated human RBC.

To manufacture the reference material of this invention, the disclosed components can be combined at ratios, which would result in hematology parameters below, at, and above medical decision points. The resulting composition can then mixed and filled in appropriate containers (vials and tubes). These containers can then be capped and labeled and stored at recommended storage condition of about 2-8° C. The reference material can be tested on various hematology parameters using statistically valid sampling and testing protocols, and the resulting reference values (assayed values) can be calculated based on the test results. For example, relevant hematology parameters can be drawn from Williams Hematology, $9^{th}$ edition which contains reference ranges for key blood variables from different sources (Williams Hematology, $9^{th}$ ed., McGraw Hill, 2016). Alternatively, Cheng et al. and/or Wakeman et al. provide various hematology parameters that can be used in the context of the disclosed invention.

| | Cheng et al. | Wakeman et al. |
|---|---|---|
| Study Date | 1994 | 2004 |
| No of Subjects | 3125 | 205 |
| Ethnicity | US European decent | UK |
| Hb(g/dL) Male | 13.2-16.9 | 13.7-17.2 |
| Hb (g/dL) Female | 10.7-15.1 | 12.0-15.2 |
| Hct(%)M | 39-50 | 40-50 |
| Hct(%)F | 34-45 | 37-46 |
| MCV (fL) M | 79-97 | 83-98 |
| MCV (fL) F | 77-97 | 85-98 |
| WBC (×10³/µL) M | 4.1-11.7 | 3.6-9.2 |
| WBC (×10³/µL) F | 4.3-12 | |
| Neutrophils (×10³/µL | 2.7-8.1 | 1.7-6.2 |
| Neutrophils (×10³)/µL M | 2.5-6.9 | |
| Lymphocytes (×10³/µL) M | 1.1-3.7 | 1.0-3.4 |
| Lymphocytes (×10³/µL) F | 1.2-3.7 | |
| Monocytes (×10³/µL) M | .013-0.86 | 0.2-0.8 |
| Monocytes (×10³/µL) F | 0.11-0.78 | |
| Platelets (×10³/µL) M | 161-385 | 140-320 |
| Platelets (×10³/µL) F | 178-434 | 180-380 |

Red Blood Cell Component

In a first aspect of the invention, the HRM comprises a biological component, a synthetic component or a combination of the biological component and synthetic component corresponding to human erythrocytes. In one aspect of the invention, the HRM comprises separated and washed human erythrocytes (hRBC) that are fixed with low concentration of a crosslinking agent, such as glutaraldehyde. In this embodiment, hRBC are washed with a physiologic buffer, such as a sodium citrate or phosphate buffered saline solution. In certain embodiments, the physiologic buffer is isotonic. After washing, the hRBC component can be resuspended in a physiologic buffer, for example sodium citrate and fixed with glutaraldehyde. Glutaraldehyde can be added to the resuspended hRBC in an amount that ranges between about 0.01 and about 0.1% (v/v). In certain embodiments, glutaraldehyde is added in an amount of about 0.05% v/v to the resuspended hRBC. The hRBC are maintained in the buffer/glutaraldehyde solution for a period of about 10 minutes to about 360 minutes. In certain embodiments, the hRBC are maintained in the buffer/glutaraldehyde solution for a period of about 100 to about 180 minutes or a period of about 120 minutes. After fixation, the hRBC are separated from the buffer/glutaraldehyde solution and resuspended in another buffer, for example the buffer identified herein as Fluid 23 (Table 1). In some embodiments, the hRBC resuspended in Fluid 23 can be stored at a temperature of about 2° C. to about 8° C. for a period of about 12 hours to about 24 hours or about 16 hours to about 20 hours. After this storage period, the hRBC are separated from Fluid 23, resuspended in Fluid 23 and adjusted to the following cell number targets:

| hRBC adjustment targets | | |
|---|---|---|
| MCV | Red Blood Cell Target | Red Blood Cell Range |
| ≤82 | 2.75 × 10⁶/µL | 2.50 × 10⁶/µL-3.00 × 10⁶/µL |
| 83-87 | 4.65 × 10⁶/µL | 4.45 × 10⁶/µL-4.85 × 10⁶/µL |
| ≥88 | 6.00 × 10⁶/µL | 5.70 × 10⁶/µL-6.30 × 10⁶/µL |

TABLE

| Component | per L |
|---|---|
| Fluid 25 | |
| BSA | 4 g |
| Citric acid | 0.75 g |
| MOPS | 2 g |
| Adenine | 0.04 g |
| Inosine | 0.08 g |
| Amikacin/Gentamycin | 0.1/0.1 g |
| Sodium chloride | 7 |
| Lactose/dextrose | 25/1 g |
| Sodium hydroxide | 0.7 g |
| ProClin ™ 150 | 0.4 mL |
| pH 7.2 ± 0.05 | |

For Fluid 23, 3.5% V/V ethanol is added to the components making up Fluid 25

In another embodiment, the HRM comprises tuned hydrogel particles similar in size (diameter and volume) to human red blood cells (hRBC) containing hemoglobin. The tuned hRBC hydrogel particles exhibit FSC and SSC parameters that are substantially similar to hRBC containing hemoglobin. Tuned hydrogel particles corresponding to hRBC can be made according to the methods disclosed in U.S. Pat. No. 9,714,897, the disclosure of which is hereby incorporated by reference in its entirety.

Platelet Component:

In a second aspect of the invention, the HRM comprises a biological component, a synthetic component or a combination of the biological component and synthetic component corresponding to human platelets. In one embodiment, the HRM comprises separated and washed goat erythrocytes fixed with high concentration of a crosslinking agent, such as glutaraldehyde. In this embodiment, Goat erythrocytes are separated and washed in a physiologic buffer, such as a sodium citrate or phosphate buffered saline solution. In certain embodiments, the physiologic buffer is isotonic.

After washing, hematocrit is measured according to methods known in the art and, if necessary, the cells are adjusted to a hematocrit level between about 44% and about 46%. The washed cells are then lysed with deionized water or an erythrocyte lysing solution. After lysing is completed, the cell suspension can be transferred into a container. The container comprising the lysed goat erythrocytes can then be immersed in a water bath at a temperature between about 30 and about 45° C., for example, about 40° C. and maintained at this temperature for about 120 minutes to about 240 minutes, for example about 180 minutes. The cells can be allowed to cool to room temperature and then stored at about 2° C. to about 8° C. for about 8 to about 12 hours. Alpha-naphthol (a-N) is then added in an amount that ranges between about 15% and about 25% v/v, for example in an amount that is about 20% v/v. The α-N treated cells are then incubated at room temperature for about 60 to about 180 minutes, preferably about 120 minutes. Glutaraldehyde is then added to the α-N treated cells in an amount that ranges between about 35% to about 50% (v/v) to form a first fixation solution. The cells treated with glutaraldehyde and α-N are then incubated at room temperature for about 90 minutes to about 180 minutes, for example, about 90 minutes to about 120 minutes. After this treatment, the cells are separated from the fixation solution (the α-N/glutaraldehyde solution) and washed with a physiologic buffer, isotonic buffer, or with deionized water. After washing of the cells, the cells can be resuspended in a physiologic buffer, isotonic buffer, or with deionized water. These resuspended cells are then treated with a second volume of glutaraldehyde (the second fixation solution) that ranges between about 10% and about 25% (v/v), for example about 15% v/v for a period of about 48 hours to about 175 hours, for example, about 40 hours to about 150 hours. The cells are then separated from the second fixation solution and washed with a wash suspension fluid and stored at room temperature, protected from light. The treated goat erythrocytes (platelet analogs) can be stored for up to about 18 months, for example, about 12 months at a temperature of about 2° C. to about 8° C. The platelet solution can be added to the HRM in an amount that provides between about $50 \times 10^3$ and about $80 \times 10^3$ platelets/µL.

In another embodiment, the HRM comprises tuned hydrogel particles similar in size (diameter and volume) to platelets, particularly human platelets. The tuned hRBC hydrogel particles exhibit FSC and SSC parameters that are substantially similar to platelets. Tuned hydrogel particles corresponding to platelets can be made according to the methods disclosed in U.S. Pat. No. 9,714,897, the disclosure of which is hereby incorporated by reference in its entirety.

Reticulocyte Component:

In a third aspect of the invention, the HRM comprises a biological component, a synthetic component or a combination of the biological component and synthetic component corresponding to human reticulocytes. In one embodiment, the HRM comprises separated and washed human erythrocytes encapsulated with RNA which represents the reticulocyte component found in whole blood. The erythrocytes can be encapsulated using various encapsulation processes, such as reversible osmotic lysis or electroporation, followed by soft glutaraldehyde fixation. Methods of preparing the reticulocyte component are known in the art (see, for example, U.S. Pat. No. 5,432,089 or Ebrahim and Ryan, 1996, Cytometry, 25:156-163, each of which is hereby incorporated by reference in its entirety).

In another embodiment, the HRM comprises tuned hydrogel particles similar in size (diameter and volume) to reticulocytes containing RNA or tagged with a fluorescence dye used in reticulocyte testing. The tuned hydrogel particles exhibit FSC and SSC parameters that are substantially similar to reticulocytes. Tuned hydrogel particles corresponding to reticulocytes can be made according to the methods disclosed in U.S. Pat. No. 9,714,897, the disclosure of which is hereby incorporated by reference in its entirety.

Lymphocyte Component:

In a fourth aspect of the invention, the HRM comprises a biological component, a synthetic component or a combination of the biological component and synthetic component corresponding to human lymphocytes. In one embodiment, separated and washed human avian, reptile or fish to represent the lymphocyte component found in a biological sample, such as human whole blood samples. The erythrocytes can be treated with a high concentration of a crosslinking agent, such as glutaraldehyde. Methods of preparing the lymphocyte component are known in the art (see, for example, U.S. Pat. No. 5,320,964 or US 2010/0086962, each or which is hereby incorporated by reference in its entirety.

In another embodiment, the HRM comprises tuned hydrogel particles similar in size (diameter and volume) to lymphocytes, particularly human lymphocytes. The tuned hydrogel particles exhibit FSC and SSC parameters that are substantially similar to lymphocytes. The tuned hydrogel particles may have additional optical properties or surface properties that are substantially similar to lymphocytes, particularly human lymphocytes. Tuned hydrogel particles corresponding to lymphocytes can be made according to the methods disclosed in U.S. Pat. No. 9,714,897, the disclosure of which is hereby incorporated by reference in its entirety.

Monocyte Component:

In a fifth aspect of the invention, the HRM comprises a biological component, a synthetic component or a combination of the biological component and synthetic component corresponding to human monocytes. In another embodiment, the HRM comprises a monocyte component that comprises separated and washed red blood cells from avian animals, such as turkey, chicken, duck, and goose red blood cells or red blood cells from non-human vertebrates including fish, particularly members of the shark family, and reptiles, such as alligators that are fixed with a crosslinking agent, such as glutaraldehyde. In a preferred embodiment, turkey erythrocytes are used to provide the monocyte component. Methods of preparing the monocyte component are known in the art (see, for example, U.S. Pat. No. 5,320,964, which is hereby incorporated by reference in its entirety).

In another embodiment, the HRM comprises tuned hydrogel particles similar in size (diameter and volume) to monocytes, particularly human monocytes. The tuned hydrogel particles exhibit FSC and SSC parameters that are substantially similar to monocytes. The tuned hydrogel particles may have additional optical properties and/or surface properties that are substantially similar to monocytes, particularly human monocytes. Tuned hydrogel particles corresponding to monocytes can be made according to the methods disclosed in U.S. Pat. No. 9,714,897, the disclosure of which is hereby incorporated by reference in its entirety.

Basophil Component:

In a sixth aspect of the invention, the HRM comprises a biological component, a synthetic component or a combination of the biological component and synthetic component corresponding to human basophils. In another embodiment, the HRM comprises tuned hydrogel particles similar in size (diameter and volume) to basophils, particularly human basophils. The tuned hydrogel particles exhibit FSC and SSC parameters that are substantially similar to basophils. The tuned hydrogel particles may have additional optical properties and/or surface properties that are substantially similar to basophils, particularly human basophils. The hydrogel particles are similar in size to human basophils. The tuned hydrogel particles may have additional optical properties or surface properties that are substantially similar to basophils, particularly human basophils. Tuned hydrogel particles corresponding to basophils can be made according to the methods disclosed in U.S. Pat. No. 9,714,897, the disclosure of which is hereby incorporated by reference in its entirety.

Neutrophil Component:

In a seventh aspect of the invention, the HRM comprises a biological component, a synthetic component or a combination of the biological component and synthetic component corresponding to human neutrophils. In one embodiment, the HRM comprises a neutrophil component that comprises separated and washed red blood cells from avian animals, such as turkey, chicken, duck, and goose red blood cells or red blood cells from non-human vertebrates including fish, particularly members of the shark family, and reptiles, such as alligators that are fixed with a crosslinking agent, such as glutaraldehyde. In a preferred embodiment, alligator erythrocytes are used to provide the neutrophil component. Methods of preparing the neutrophil component are known in the art (see, for example, U.S. Pat. No. 5,320,964, which is hereby incorporated by reference in its entirety).

In another embodiment, the HRM comprises tuned hydrogel particles similar in size (diameter and volume) to neutrophils, particularly human neutrophils. The tuned hydrogel particles exhibit FSC and SSC parameters that are substantially similar to neutrophils. The tuned hydrogel particles may have additional optical properties and/or surface properties that are substantially similar to neutrophils, particularly human neutrophils. Tuned hydrogel particles corresponding to neutrophils can be made according to the methods disclosed in U.S. Pat. No. 9,714,897, the disclosure of which is hereby incorporated by reference in its entirety.

Eosinophil Component:

In an eighth aspect of the invention, the HRM comprises a biological component, a synthetic component or a combination of the biological component and synthetic component corresponding to human eosinophils. In one embodiment, the HRM comprises an eosinophil component that comprises separated and washed red blood cells from avian animals, such as turkey, chicken, duck, and goose red blood cells or red blood cells from non-human vertebrates including fish, particularly members of the shark family, and reptiles, such as alligators that are fixed with a crosslinking agent, such as glutaraldehyde. In a preferred embodiment, alligator erythrocytes are used to provide the eosinophil component. Methods of preparing the eosinophil component are known in the art (see, for example, U.S. Pat. No. 5,320,964, which is hereby incorporated by reference in its entirety).

In another embodiment, the HRM comprises tuned hydrogel particles similar in size (diameter and volume) to eosinophils, particularly human eosinophils. The tuned hydrogel particles exhibit FSC and SSC parameters that are substantially similar to eosinophils. The tuned hydrogel particles may have additional optical properties and/or surface properties that are substantially similar to eosinophils, particularly human eosinophils. Tuned hydrogel particles corresponding to eosinophils can be made according to the methods disclosed in U.S. Pat. No. 9,714,897, the disclosure of which is hereby incorporated by reference in its entirety.

Immature Reticulocyte Component:

In a ninth aspect of the invention, the HRM comprises a biological component, a synthetic component or a combination of the biological component and synthetic component corresponding to immature human reticulocytes. In one embodiment, the HRM comprises separated and washed human erythrocytes encapsulated with RNA which represents the immature reticulocyte component found in whole blood. The erythrocytes can be encapsulated using various encapsulation processes, such as reversible osmotic lysis or electroporation, followed by soft glutaraldehyde fixation. Methods of preparing the immature reticulocyte component are known in the art (see, for example, U.S. Pat. No. 5,432,089 or Ebrahim and Ryan, 1996, Cytometry, 25:156-163), each of which is hereby incorporated by reference in its entirety).

In another embodiment, the HRM comprises tuned hydrogel particles similar in size (diameter and volume) to immature reticulocytes, particularly immature human reticulocytes. The tuned hydrogel particles exhibit FSC and SSC parameters that are substantially similar to immature reticulocytes. The tuned hydrogel particles may have additional optical properties and/or surface properties that are substantially similar to immature reticulocytes, particularly immature human reticulocytes. Tuned hydrogel particles corresponding to immature reticulocytes can be made according to the methods disclosed in U.S. Pat. No. 9,714,897, the disclosure of which is hereby incorporated by reference in its entirety. Further, hydrogel particles similar in size to immature reticulocytes (e.g., immature human reticulocytes) can contain large amount of RNA or be labeled with common dyes used for reticulocyte analysis.

Immature Granulocyte Component:

In a tenth aspect of the invention, the HRM comprises a biological component, a synthetic component or a combination of the biological component and synthetic component corresponding to immature human granulocytes. In one embodiment, the HRM comprises an immature granulocyte component that comprises separated and washed red blood cells from avian animals, such as ostrich or emu red blood cells or red blood cells from non-human vertebrates including fish, particularly members of the shark family, and reptiles, such as alligators that are fixed with a crosslinking agent, such as glutaraldehyde. In a preferred embodiment, alligator erythrocytes are used to provide the immature granulocyte component. Methods of preparing the immature granulocyte component are known in the art (see, for example, U.S. Pat. No. 7,109,036, which is hereby incorporated by reference in its entirety).

In another embodiment, the HRM comprises tuned hydrogel particles similar in size (diameter and volume) to immature granulocytes, particularly immature human granulocytes. The tuned hydrogel particles exhibit FSC and SSC parameters that are substantially similar to immature granulocytes. The tuned hydrogel particles may have additional optical properties and/or surface properties that are substantially similar to immature granulocytes, particularly immature human granulocytes. Tuned hydrogel particles corresponding to immature granulocytes can be made according to the methods disclosed in U.S. Pat. No. 9,714,897, the disclosure of which is hereby incorporated by reference in its entirety.

Immature Thrombocyte Component:

In an eleventh aspect of the invention, the HRM comprises a biological component, a synthetic component or a combination of the biological component and synthetic component corresponding to immature human thrombocytes. In one embodiment, the HRM comprises separated and washed goat erythrocytes fixed with high concentration of a crosslinking agent, such as glutaraldehyde as a reference material for immature thrombocytes. This component is prepared in a manner similar to that disclosed with respect to platelets, supra. The optical properties substantially similar to human immature thrombocytes, are similar in size to immature human thrombocytes a containing nucleic acid or are labeled with common dyes used for immature thrombocyte analysis.

In another embodiment, the HRM comprises tuned hydrogel particles similar in size (diameter and volume) to immature thrombocytes, particularly immature human thrombocytes. The tuned hydrogel particles exhibit FSC and SSC parameters that are substantially similar to immature thrombocytes. The tuned hydrogel particles may have additional optical properties and/or surface properties that are substantially similar to immature thrombocytes, particularly immature human thrombocytes. Tuned hydrogel particles corresponding to immature thrombocytes can be made according to the methods disclosed in U.S. Pat. No. 9,714,897, the disclosure of which is hereby incorporated by reference in its entirety. Further, hydrogel particles similar in size to immature thrombocytes (e.g., immature human thrombocytes) can contain large amount of RNA or be labeled with common dyes used for reticulocyte analysis.

Nucleated Red Blood Cell Component:

In a twelfth aspect of the invention, the HRM comprises a biological component, a synthetic component or a combination of the biological component and synthetic component corresponding to nucleated human RBC. In one embodiment, the HRM comprises separated and washed avian (e.g., chicken or turkey) erythrocytes fixed with high concentration of a crosslinking agent, such as glutaraldehyde as a reference material for nucleated RBC. Methods of preparing the nucleated RBC component are known in the art (see, for example, U.S. Pat. No. 6,406,915, which is hereby incorporated by reference in its entirety).

In another embodiment, the HRM comprises tuned hydrogel particles similar in size (diameter and volume) to nucleated red blood cells, particularly human nucleated red blood cells. The tuned hydrogel particles exhibit FSC and SSC parameters that are substantially similar to nucleated red blood cells. The tuned hydrogel particles may have additional optical properties and/or surface properties that are substantially similar to nucleated red blood cells, particularly human nucleated red blood cells. Tuned hydrogel particles corresponding to nucleated red blood cells can be made according to the methods disclosed in U.S. Pat. No. 9,714,897, the disclosure of which is hereby incorporated by reference in its entirety.

Crosslinking Agent

The crosslinking agent may be any suitable crosslinking agent, including but not limited to those including an aldehyde, oxazolidine, alcohol, cyclic urea, or the like. Examples include, without limitation, formaldehyde, paraformaldehyde, glutaraldehyde, diazolidinyl urea (DU), imidazolidinyl urea (IDU), dimethylol urea, dimethlol-5,5-dimethylhydantoin, 2-bromo-2-nitropropane-1,3-diol; quaternary adamantine,-hydroxymethyl-1-aza 3,7-dioxabicyclo (3.3.0) octane and 5-hydroxymethyl-1-aza-3,7-dioxabicyclo (3.3.0) octane and 5-hydroxypoly-methyleneoxy-methyl-1-aza-3,7-dioxabicyclo (3.3.0) octane, sodium hydroxmethyl glycinate, and mixtures thereof, and or the like.

Hydrogel Particles:

In one aspect, a composition comprising a plurality of hydrogel particles is provided that serves as a HRM. In this aspect of the invention, the individual hydrogel particles of each plurality has one or more optical properties substantially similar to one or more optical properties of a target cell. As discussed above, in one aspect, the present invention provides individual hydrogel particles each having one or more optical properties substantially similar to one or more optical properties of a target cell. In one embodiment, the one or more optical properties, is a side scatter profile, a forward scatter profile or a secondary marker profile, such as a fluorescence marker profile, for example a fluorescence marker profile of a fluorescently-labeled antibody that binds to the surface of the hydrogel particle to which a surface marker associated with a particular target cell. "Substantially similar," as used herein, denotes at least 40% similar, at least 50% similar, at least 60% similar, at least 70% similar, at least 80% similar, at least 90% similar, at least 95% similar, at least 96% similar, at least 97% similar, at least 98% similar or at least 99% similar to a specific cell type (such as a human RBC, neutrophil, basophil, lymphocyte, platelet, etc.).

As disclosed in U.S. Pat. No. 9,714,897, one or more of the hydrogel particles can be functionalized to mimic one or more optical property and/or one or more cell surface property of a target cell or a labeled target cell, functionalized with one or more fluorescent dyes (as disclosed in columns 17-30 of the '897 patent), functionalized with one or more cell surface markers (or epitope binding regions thereof) as set forth in Tables 4, 7 and/or 8 of the '897 patent, or a combination thereof. In various other embodiments, the hydrogel particles can further comprise blood group antigens, such as those discussed below and/or antigen D (RhD), which carries the major antigen of the RH system. For example, the hydrogel particles can be polymerized with at least one bifunctional monomer which can then be used to attach a cell surface marker, blood group antigen, an epitope binding region of a cell surface marker, a fluorescent dye, or any combination thereof to the particle to confer a desired optical and/or cell surface property. The free functional group can be an amine group, a carboxyl group, or a hydroxyl group. Depending on the functionalization desired, it is to be understood that multiple bifunctional monomers can be used, for example, to functionalize the particle using different chemistries and with different elements (e.g., fluorescent dyes or cell surface markers). Cell surface markers associated with the cells that comprise the HRM are known in the art.

Exemplary blood group antigen oligosaccharides include the following: Blood group A antigen: GalNacα1,3(Fucα1,2)Galβ1,3GlcNAcβ1-R; Blood group B antigen: Galα1,3(Fucα1,2)Galβ1,3 GlcNAcβ1-R, Blood group 0 antigen: Fucα1,2Galβ1,3G1cNAcβ1-R, Wherein R represents a polypeptide or a point of attachment when the blood group antigen is linked to a hydrogel particle. Other exemplary blood group antigens include the antigens of the Rh (rhesus) blood group system, such as antigen D (RhD; see Le van et al., *PNAS*, 1992, 89(22):10925-10929, the disclosure or which is hereby incorporated by reference in its entirety).

In yet another aspect, a method of calibrating a cytometric device for analysis of a target cell is provided. In one embodiment, the method comprises (a) inserting into the device a HRM having optical properties substantially similar to the optical properties to target cells found in a biological sample (for example, human whole blood); b) measuring the optical properties of the HRM using the cytometric device, thereby calibrating the cytometric device for analysis of a biological sample. Cytometric devices are known in the art, and include commercially available devices for performing flow cytometry and FACS.

All patents, patent applications, provisional applications, and publications referred to or cited herein are incorporated by reference in their entirety, including all figures and tables, to the extent they are not inconsistent with the explicit teachings of this specification.

Following are examples which illustrate procedures for practicing the invention. These examples should not be construed as limiting. All percentages are by weight and all solvent mixture proportions are by volume unless otherwise noted.

Example 1

Presented in FIG. 5 is the hematology report generated using Abbott Cell-Dyn Emerald Hematology Analyzer for a typical HRM of this invention. The HRM was prepared by adding synthetic particles that simulate human leukocytes in size and morphology and stabilized goat erythrocytes that simulate human thrombocytes in size and morphology to the stabilized human erythrocytes suspended in an isotonic and pH-neutral buffered aqueous fluid. The sample prepared by the combination of these components resulted in a HRM that provided 16 parameters including 3-part white blood cell populations (WBC, LYM, MID, GRA, LYM %, MID %, GRA %, RBC, HGB, HCT, MCV, MCH, MCHC, RDW, PLT, and MPV).

To prepare the above quality control material, human red blood cells were washed in a pH 7.0 citrate buffer, fixed with 0.024% glutaraldehyde for two hours at room temperature, washed once in stabilizing buffer, and then held at 2-8° C. until use. To manufacture the platelet (PLT) analog, goat red blood cells were washed in an isotonic saline solution, then exposed to hypotonic conditions between 40° C. and 42° C. while mixing for 3 hours, cooled for approximately one hour at room temperature, and then stored overnight at 2-8° C. After this step, the goat red blood cells were exposed to 3 successive treatment steps of 3.9% alpha-naphthol, 10.2% glutaraldehyde, and 0.009% glutaraldehyde for 2 hours, 2 hours, and 48 hours at room temperature respectively to fix the cells. Finally, the processed goat red blood cells were washed once with the stabilizing solution and then allowed to equilibrate at room temperature protected from light for 7 days.

Both the fixed human RBCs and fixed goat RBCs were re-suspended in an isotonic fluid containing synthetic WBCs. The concentrations of these components were adjusted to approximately $2 \times 10^6$ RBCs/µL, $50 \times 10^3$ PLTs/ µL, and $3.3 \times 10^3$ synthetic WBCs/µL by concentrating the cellular components with centrifugation or diluting the cellular components with the isotonic suspension fluid followed by testing using an automated hematology analyzer. Synthetic white blood cells were purchased from Slingshot Biosciences, Emeryville, California (FlowCytes®, product number: SSBS-004-A). These three components were mixed at the volume ratios of 0.6 RBCs: 0.230 WBCs: 0.0023 PLTs: 0.17 isotonic buffer to prepare the HRM of this invention as depicted in FIG. 5.

Figure 6:
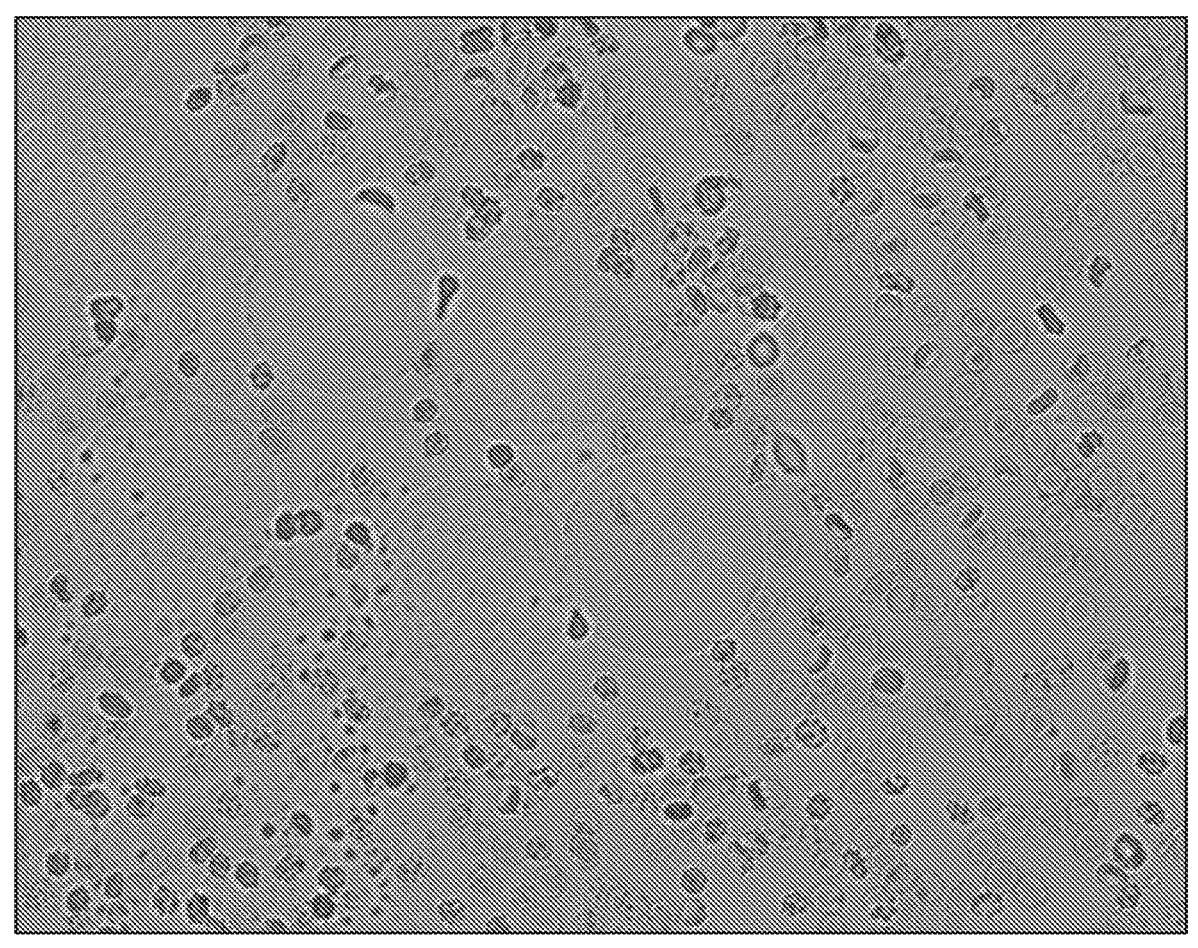
FIG. 6 is a photomicrograph of the sample of the HRM of this invention.

Presented in FIG. 6 is a photomicrograph of the sample of the HRM of this invention. This photomicrograph was obtained using an Olympus BX43 Microscope equipped with 400× magnification. A new methylene blue stain was used to enhance contrast between the red cells and hydrogel spheres. Microscopic examination of the material showed that these synthetic particles (large round particles in the photomicrograph) are compatible with human and animal blood components in a HRM and do not result in aggregation or adhesion of cellular components. Furthermore, they stain similarly to WBCs and do not interfere with staining properties of other components.

A limited single-temperature accelerated stability study was performed on the HRM of this invention to observe product performance and stability issues faster than that observed during a real time stability study. For this accelerated stability study, samples of the quality control were stored at 35° C. for 7 days and tested on Abbott Cell-Dyn Emerald. Presented in Table 1 are the Day 0 and Day 7 test results for all parameters. It should be pointed out that for a chemical reagent, storage of product at 35° C. for ~10 days is equivalent of storage of the product at 5° C. for 1 year (based on an activation energy of 20K Cal/mole model). The data presented in Table 2 predict that the HRM of this invention can have a shelf life of greater than 9 months if stored at 2-8° C.

TABLE 2

| Limited Accelerated Stability Study at 35° C. | | | |
|---|---|---|---|
| Parameter | Units | Day 0 | Day 7 |
| WBC | $10^3$/µL | 3.3 | 3.3 |
| LYM | $10^3$/µL | 0.30 | 0.30 |
| MID | $10^3$/µL | 0.0 | 0.0 |
| GRAN | $10^3$/µL | 3.0 | 3.0 |
| LYM % | % | 8.7 | 6.9 |
| MID % | % | 0.4 | 0.5 |
| GRAN % | % | 91.0 | 92.6 |
| RBC | $10^6$/µL | 2.07 | 2.10 |
| HGB | g/dL | 5.7 | 6.0 |
| HCT | % | 16.5 | 16.7 |
| MCV | fL | 79.3 | 77.5 |
| MCH | pg | 27.3 | 27.9 |
| MCHC | g/dL | 34.4 | 36.1 |
| RDW | % | 14.2 | 17.1 |
| PLT | $10^3$/µL | 42 | 52 |
| MPV | fL | 9.4 | 8.9 |

Example 2

In this prophetic example, the HRM of this invention is prepared by full usage of the hydrogel particles in the suspension fluid. The sample prepared by the combination of these components would result in a HRM that provides over 20 parameters including 5-part white blood cell populations (WBC, LYM, MONO, EO, NEUT, BASO, LYM %, MONO %, EO %, NEUT %, BASO %, IG, RBC, HGB, HCT, MCV, MCH, MCHC, RDW, PLT, MPV, RETIC, RETIC %, and other related parameters).

The HRM will have the following components at concentrations:

Suspension Fluid (pH neutral and isotonic);

Hydrogel particles selectively tuned to simulate Red Blood Cells ($1 \times 10^{12}$ to $7 \times 10^{12}$/L);

Hydrogel particles selectively tuned to simulate Platelets ($50\times10^6$ to $800\times10^6$/L);

Hydrogel particles selectively tuned to simulate Reticulocytes (0.5% to 10%);

Hydrogel particles selectively tuned to simulate Lymphocytes (10 to 50%);

Hydrogel particles selectively tuned to simulate Monocytes (1 to 10%);

Hydrogel particles selectively tuned to simulate Basophils (1 to 10%);

Hydrogel particles selectively tuned to simulate Neutrophils (20 to 80%);

Hydrogel particles selectively tuned to simulate Eosinophils (1 to 10%);

Hydrogel particles selectively tuned to simulate Immature Reticulocytes (0.1 to 0.9%);

Hydrogel particles selectively tuned to simulate Immature Granulocytes (0.2 to 7.0%);

Hydrogel particles selectively tuned to simulate Immature Thrombocytes (1 to 5%); and Hydrogel particles selectively tuned to simulate Nucleated Red Blood Cells (0.1 to 1%).

After combining these components and achieving the desired target levels for each hematology parameter, the cellular suspension will be filled in appropriate bottles, capped, labeled, and stored at ambient conditions. The product manufactured based on the example will produce hematology results, histograms, and scattergrams similar to those depicted in FIGS. 1, 2, 3, and 4.

Example 3

In this prophetic example, the HRM of this invention is prepared by partial usage of the hydrogel particles along with other blood cell surrogates in the suspension fluid. The sample prepared by the combination of these components would result in a HRM that provides over 20 parameters including 5-part white blood cell populations (WBC, LYM, MONO, EO, NEUT, BASO, LYM %, MONO %, EO %, NEUT %, BASO %, IG, RBC, HGB, HCT, MCV, MCH, MCHC, RDW, PLT, MPV, RETIC, RETIC %, and other related parameters).

The HRM will have the following components at concentrations:

Suspension Fluid (pH neutral and isotonic);

Soft fixed human Red Blood Cells ($1\times10^{12}$ to $7\times10^{12}$/L);

Hard fixed goat red blood cells to simulate Platelets ($50\times10^6$ to $800\times10^6$/L);

RNA-encapsulated human red blood cells to simulate Reticulocytes (0.5% to 10%);

Hydrogel particles selectively tuned to simulate Lymphocytes (10 to 50%);

Hydrogel particles selectively tuned to simulate Monocytes (1 to 10%);

Hydrogel particles selectively tuned to simulate Basophils (1 to 10%);

Hydrogel particles selectively tuned to simulate Neutrophils (20 to 80%);

Hydrogel particles selectively tuned to simulate Eosinophils (1 to 10%);

Hydrogel particles selectively tuned to simulate Immature Reticulocytes (0.1 to 0.9%);

Hydrogel particles selectively tuned to simulate Immature Granulocytes (0.2 to 7.0%);

Hydrogel particles selectively tuned to simulate Immature Thrombocytes (1 to 5%); and Hard fixed chicken red blood cells to simulate Nucleated Red Blood Cells (0.1 to 1%).

After combining these components and achieving the desired target levels for each hematology parameter, the cellular suspension will be filled in appropriate bottles, capped, labeled, and stored at 2-8° C. The product manufactured based on the example will product hematology results, histograms, and scattergrams similar to those depicted in FIGS. 1, 2, 3, and 4.

The following are ranges that span a typical hematology controls levels 1-3.

TABLE 3

| Range of HRMs Blood Variables | | | |
|---|---|---|---|
| Variable | Units | LL | UL |
| WBC | K/μL | 2.8 | 26.1 |
| NEUT | K/μL | 1 | 20.1 |
| NEUT | % | 40.5 | 84.6 |
| LYMPH | K/μL | 0.6 | 6.2 |
| LYMPH | % | 24.5 | 26 |
| MONO | K/μL | 0 | e1.2 |
| MONO | % | 1 | 6 |
| EOS | K/μL | 0 | 1.8 |
| EOS | % | 0 | 8.4 |
| BASO | K/μL | 0 | 0.6 |
| BASO | % | 0 | 2.4 |
| RBC | M/μL | 1.99 | 5.49 |
| HGB | g/dL | 5.1 | 17.2 |
| HCT | % | 13.6 | 46.2 |
| MCV | fL | 66 | 87 |
| MCH | pg | 22.5 | 33.9 |
| MCHC | g/dL | 32.1 | 41.4 |
| RDW | % | 10.8 | 13 |
| PLT | K/μL | 53 | 555 |
| MPV | fL | 2.5 | 8 |
| NRBC | K/μL | 0 | 5.5 |

These ranges were generated from a typical commercially available hematology control (RDS Heme A L1-L3 control ranges (insert)).
LL = lower limit of level 1 [mean − (1/2 × range)]
UL = upper limit of level 3 [mean + (1/2 × range)]

Example 4

In this prophetic example, the different HRM of this invention are prepared by partial usage of the hydrogel particles along with other blood cell surrogates in the suspension fluid. In this example, a first HRM that includes hydrogel particles comprising blood group antigen A and RhD (on the same or different hydrogel particles), a second HRM that includes hydrogel particles comprising blood group antigen B and RhD (on the same or different hydrogel particles), a third HRM that includes hydrogel particles comprising blood group antigen A and does not include RhD, and a fourth HRM that includes hydrogel particles comprising blood group antigen B and does not include RhD. These HRM can be used as positive controls for blood typing assays. The samples prepared by the combination of these components would result in a HRM that provides over 20 parameters including 5-part white blood cell populations (WBC, LYM, MONO, EO, NEUT, BASO, LYM %, MONO %, EO %, NEUT %, BASO %, IG, RBC, HGB, HCT, MCV, MCH, MCHC, RDW, PLT, MPV, RETIC, RETIC %, and other related parameters) and hydrogel particles permitting blood typing.

The each HRM is contacted with a sample comprising antibodies specific for each blood type (anti-A, anti-B and anti-RhD antibodies) and observed for agglutination of the hydrogel particles. A positive reaction is observed when the antibody causes agglutination of hydrogel particles comprising one of the blood group antigens.

It should be understood that the actual and prophetic examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated within the scope of the invention without limitation thereto.

REFERENCES

Cheng, C K, Chan J, Cembrowski G S, van Assendelft O W, Complete blood count reference interval diagrams derived from NHANES iii; Stratification by age, sex, and race. Lab Hematology 10:42-53, 2004.

Wakeman L, Al-Ismail S, Benton A, et al.: Robust routine hematology reference ranges for healthy adults. Int J lab Hematology 29:279-283, 2007.

We claim:

1. A hematology reference material (HRM) comprising a suspension fluid and:
   a red blood cell (RBC) component that comprises human erythrocytes fixed with a crosslinking agent;
   a platelet component that comprises goat erythrocytes fixed with a crosslinking agent;
   a reticulocyte component that comprises fixed human erythrocytes encapsulated with RNA;
   a lymphocyte component that comprises chicken erythrocytes fixed with a crosslinking agent;
   a monocyte component that comprises turkey erythrocytes fixed with a crosslinking agent;
   a basophil component that comprises alligator erythrocytes fixed with a crosslinking agent;
   a neutrophil component that comprises alligator erythrocytes fixed with a crosslinking agent;
   an eosinophil component that comprises alligator erythrocytes fixed with a crosslinking agent;
   an immature reticulocyte component that comprises fixed human erythrocytes encapsulated with RNA;
   an immature granulocyte component that comprises alligator erythrocytes fixed with a crosslinking agent;
   an immature thrombocyte component that comprises goat erythrocytes fixed with a crosslinking agent; and
   a nucleated red blood cell component that comprises chicken erythrocytes fixed a crosslinking agent,
   wherein each of said components exhibit a forward scatter profile or a side scatter profile that is at least 95% similar to its corresponding component in a human blood sample.

2. The HRM according to claim 1, wherein the suspension fluid is an aqueous isotonic solution with a pH of 7.0 to about 7.6 and containing additives selected from anti-microbial agents, surfactants, stabilizers, buffers, salts, enzyme inhibitors, albumin, and lipoproteins.

3. The HRM according claim 1, said HRM further comprising hydrogel particles comprising blood group antigens.

4. The HRM according to claim 3, wherein said HRM comprises a population of hydrogel particles comprising blood group antigen A, a population of hydrogel particles comprising blood group antigen B, a population of hydrogel particles comprising blood group antigen RhD, or a combination of said populations of hydrogel particles.

5. The HRM according to claim 4, wherein the population of hydrogel particles comprises blood group antigen A and blood group antigen RhD attached to the hydrogel particles.

6. The HRM according to claim 4, wherein the population of hydrogel particles comprises blood group antigen B and blood group antigen RhD attached to the hydrogel particles.

7. The HRM according to claim 4, wherein the population of hydrogel particles comprising blood group antigen A does not comprise blood group antigen RhD attached to the hydrogel particles.

8. The HRM according to claim 4, wherein the population of hydrogel particles comprising blood group antigen B does not comprise blood group antigen RhD attached to the hydrogel particles.

9. A method of agglutinating a HRM containing hydrogel particles comprising blood group antigens comprising contacting an HRM according to claim 3 with antibodies specific to blood group antigens and agglutinating the hydrogel particles in said HRM.

10. The method according to claim 9, wherein said HRM comprises a population of hydrogel particles comprising blood group antigen A, a population of hydrogel particles comprising blood group antigen B, a population of hydrogel particles comprising blood group antigen RhD, or a combination of said populations of hydrogel particles.

11. The method according to claim 10, wherein the population of hydrogel particles comprises blood group antigen A and blood group antigen RhD attached to the hydrogel particles.

12. The method according to claim 10, wherein the population of hydrogel particles comprises blood group antigen B and blood group antigen RhD attached to the hydrogel particles.

13. The method according to claim 10, wherein the population of hydrogel particles comprising blood group antigen A does not comprise blood group antigen RhD attached to the hydrogel particles.

14. The method according to claim 10, wherein the population of hydrogel particles comprising blood group antigen B does not comprise blood group antigen RhD attached to the hydrogel particles.

15. The HRM according to claim 1, wherein the HRM comprises a white blood cell count (WBC), a red blood cell count (RBC), a platelet count (PLT), a hemoglobin concentration (HGB), a red cell distribution width (RDW), a platelet distribution width (PDW), a hematocrit (HCT), a mean cell volume (MCV), a mean platelet volume (MPV), a eosinophil count (EOS), a eosinophil percent (EOS %), a basophil count (BASO), a basophil percent (BASO %), a monocyte count (MONO), a monocyte percent (MONO %), a lymphocyte count (LYM), a lymphocyte percent (LYM %), a reticulocyte count (RETIC), a reticulocyte percent (RETIC %), and nucleated red blood cells (NRBC), the components having a lower limit (LL) and upper limit (UL) as follows:

| Range of HRMs Blood Variables | | | |
|---|---|---|---|
| Variable | Units | LL | UL |
| WBC | K/µL | 2.8 | 26.1 |
| NEUT | K/µL | 1 | 20.1 |
| NEUT | % | 40.5 | 84.6 |
| LYMPH | K/µL | 0.6 | 6.2 |
| LYMPH | % | 24.5 | 26 |
| MONO | K/µL | 0 | e1.2 |

-continued

Range of HRMs Blood Variables

| Variable | Units | LL | UL |
|---|---|---|---|
| MONO | % | 1 | 6 |
| EOS | K/μL | 0 | 1.8 |
| EOS | % | 0 | 8.4 |
| BASO | K/μL | 0 | 0.6 |
| BASO | % | 0 | 2.4 |
| RBC | M/μL | 1.99 | 5.49 |
| HGB | g/dL | 5.1 | 17.2 |
| HCT | % | 13.6 | 46.2 |
| MCV | fL | 66 | 87 |
| MCH | pg | 22.5 | 33.9 |
| MCHC | g/dL | 32.1 | 41.4 |
| RDW | % | 10.8 | 13 |
| PLT | K/μL | 53 | 555 |
| MPV | fL | 2.5 | 8 |
| NRBC | K/μL | 0 | 5.5. |

16. A method for calibrating a cytometric device for analysis of a biological sample comprising:
inserting, into a cytometric device, a HRM according to claim 1;
measuring the side scatter, forward scatter, and hydrodynamic properties of the components of said HRM using the cytometric device; and
calibrating the cytometric device for analysis of cells in a biological sample based on the measured side scatter, forward scatter, and hydrodynamic properties of the HRM.

17. A method for determining if a sample includes one or more cell types comprising:
inserting, into a cytometric device, a HRM according to claim 1;
measuring the forward scatter, side scatter, and hydrodynamic properties of the HRM using the cytometric device;
calibrating the cytometric device based on the measured forward scatter, side scatter, and hydrodynamic properties of the HRM;
adding a sample comprising a plurality of cells to the calibrated cytometric device; and
measuring the forward scatter, side scatter, and hydrodynamic properties of each cell of the plurality of cells using the calibrated cytometric device to determine if the sample includes one or more of a specific cell type.

18. A hematology reference material (HRM) comprising a suspension fluid and:
a red blood cell (RBC) component that comprises human erythrocytes fixed with a crosslinking agent and hydrogel particles substantially similar to human red blood cells containing hemoglobin;
a platelet component that comprises goat erythrocytes fixed with a crosslinking agent and hydrogel particles substantially similar to human platelets;
a reticulocyte component that comprises fixed human erythrocytes encapsulated with RNA and hydrogel particles substantially similar to human reticulocytes;
a lymphocyte component that comprises chicken erythrocytes fixed with a crosslinking agent and hydrogel particles substantially similar to human lymphocytes;
a monocyte component that comprises turkey erythrocytes fixed with a crosslinking agent and hydrogel particles substantially similar to human monocytes;
a basophil component that comprises alligator erythrocytes fixed with a crosslinking agent and hydrogel particles substantially similar to human basophils;

a neutrophil component that comprises alligator erythrocytes fixed with a crosslinking agent and hydrogel particles substantially similar to human neutrophils;
an eosinophil component that comprises alligator erythrocytes fixed with a crosslinking agent and hydrogel particles substantially similar to human eosinophils;
an immature reticulocyte component that comprises fixed human erythrocytes encapsulated with RNA and hydrogel particles substantially similar to immature human reticulocytes;
an immature granulocyte component that comprises alligator erythrocytes fixed with a crosslinking agent and hydrogel particles substantially similar to immature human granulocytes;
an immature thrombocyte component that comprises goat erythrocytes fixed with a crosslinking agent and hydrogel particles substantially similar immature human thrombocytes; and
a nucleated red blood cell component that comprises chicken erythrocytes fixed a crosslinking agent and hydrogel particles substantially similar to nucleated human red blood cells,
wherein each of said components exhibit a forward scatter profile or a side scatter profile that is at least 95% similar to its corresponding component in a human blood sample.

19. The HRM according to claim 18, wherein each component comprises about 0.1% to about 99.9% biological component and about 0.1% to about 99.9% hydrogel component, the percentages of which total 100% for said components.

20. The HRM according to claim 18, wherein the suspension fluid is an aqueous isotonic solution with a pH of 7.0 to about 7.6 and containing additives selected from antimicrobial agents, surfactants, stabilizers, buffers, salts, enzyme inhibitors, albumin, and lipoproteins.

21. A method for calibrating a cytometric device for analysis of a biological sample comprising:
inserting, into a cytometric device, a HRM according to claim 18;
measuring the side scatter, forward scatter, and hydrodynamic properties of the components of said HRM using the cytometric device; and
calibrating the cytometric device for analysis of cells in a biological sample based on the measured side scatter, forward scatter, and hydrodynamic properties of the HRM.

22. A method for determining if a sample includes one or more cell types comprising:
inserting, into a cytometric device, a HRM according to claim 18;
measuring the forward scatter, side scatter, and hydrodynamic properties of the HRM using the cytometric device;
calibrating the cytometric device based on the measured forward scatter, side scatter, and hydrodynamic properties of the HRM;
adding a sample comprising a plurality of cells to the calibrated cytometric device; and
measuring the forward scatter, side scatter, and hydrodynamic properties of each cell of the plurality of cells using the calibrated cytometric device to determine if the sample includes one or more of a specific cell type.

23. The HRM according to claim 18, wherein the HRM comprises a white blood cell count (WBC), a red blood cell count (RBC), a platelet count (PLT), a hemoglobin concentration (HGB), a red cell distribution width (RDW), a platelet distribution width (PDW), a hematocrit (HCT), a mean cell volume (MCV), a mean platelet volume (MPV), a eosinophil count (EOS), a eosinophil percent (EOS %), a basophil count (BASO), a basophil percent (BASO %), a monocyte count (MONO), a monocyte percent (MONO %), a lymphocyte count (LYM), a lymphocyte percent (LYM %), a reticulocyte count (RETIC), a reticulocyte percent (RETIC %), and nucleated red blood cells (NRBC), the components having a lower limit (LL) and upper limit (UL) as follows:

| Range of HRMs Blood Variables | | | |
|---|---|---|---|
| Variable | Units | LL | UL |
| WBC | K/μL | 2.8 | 26.1 |
| NEUT | K/μL | 1 | 20.1 |
| NEUT | % | 40.5 | 84.6 |
| LYMPH | K/μL | 0.6 | 6.2 |
| LYMPH | % | 24.5 | 26 |
| MONO | K/μL | 0 | e1.2 |

-continued

| Range of HRMs Blood Variables | | | |
|---|---|---|---|
| Variable | Units | LL | UL |
| MONO | % | 1 | 6 |
| EOS | K/μL | 0 | 1.8 |
| EOS | % | 0 | 8.4 |
| BASO | K/μL | 0 | 0.6 |
| BASO | % | 0 | 2.4 |
| RBC | M/μL | 1.99 | 5.49 |
| HGB | g/dL | 5.1 | 17.2 |
| HCT | % | 13.6 | 46.2 |
| MCV | fL | 66 | 87 |
| MCH | pg | 22.5 | 33.9 |
| MCHC | g/dL | 32.1 | 41.4 |
| RDW | % | 10.8 | 13 |
| PLT | K/μL | 53 | 555 |
| MPV | fL | 2.5 | 8 |
| NRBC | K/μL | 0 | 5.5. |

* * * * *